United States Patent
Bergström

(10) Patent No.: US 7,160,397 B2
(45) Date of Patent: Jan. 9, 2007

(54) ALKOXYLATE MIXTURE AND ITS USE AS A CLEANING AGENT FOR HARD SURFACES

(75) Inventor: Karin Bergström, Kungälv (SE)

(73) Assignee: Akzo Nobel N.V., Arnhem (NL)

( * ) Notice: Subject to any disclaimer, the term of this patent is extended or adjusted under 35 U.S.C. 154(b) by 26 days.

(21) Appl. No.: 10/525,263

(22) PCT Filed: Jun. 19, 2003

(86) PCT No.: PCT/SE03/01049

§ 371 (c)(1),
(2), (4) Date: Feb. 22, 2005

(87) PCT Pub. No.: WO2004/005230

PCT Pub. Date: Jan. 15, 2004

(65) Prior Publication Data

US 2006/0148664 A1    Jul. 6, 2006

(30) Foreign Application Priority Data

Jul. 4, 2002    (SE) .................................. 0202100

(51) Int. Cl.
*C11D 1/722*    (2006.01)
(52) U.S. Cl. .................... 134/42; 510/421; 510/506
(58) Field of Classification Search .................... None
See application file for complete search history.

(56) References Cited

U.S. PATENT DOCUMENTS

| | | | | |
|---|---|---|---|---|
| 4,343,616 A * | 8/1982 | Decker et al. | ............... | 8/115.6 |
| 4,965,014 A | 10/1990 | Jeschke et al. | ......... | 252/174.22 |
| 5,385,681 A * | 1/1995 | Sato et al. | ..................... | 8/137 |
| 5,705,476 A | 1/1998 | Hoffarth | ..................... | 510/535 |
| 6,150,445 A * | 11/2000 | Bostrom et al. | ............. | 524/378 |
| 6,602,823 B1 * | 8/2003 | Rochling et al. | ......... | 504/116.1 |

FOREIGN PATENT DOCUMENTS

| | | | |
|---|---|---|---|
| DE | 292147 A5 * | 7/1991 | |
| EP | 0034194 B1 | 8/1981 | |
| EP | 0652281 A1 | 5/1995 | |
| EP | 0681865 B1 | 11/1995 | |
| EP | 0845449 A1 | 6/1998 | |

OTHER PUBLICATIONS

International Search Report, No. PCT/SE/03/01049, Oct. 3, 2003.
Derwent Abstract DD 292146 A5; Jul. 25, 1991.
Derwent Abstract DD 292147 A5; Jul. 25, 1991.
Derwent Abstract of EP 0034194 B1; Aug. 26, 1981.

* cited by examiner

*Primary Examiner*—John R. Hardee
(74) *Attorney, Agent, or Firm*—Ralph J. Mancini; Robert C. Morriss

(57) ABSTRACT

The invention relates to an alkoxylate mixture having formula (I) where PO is a propyleneoxy unit, EO is an ethyleneoxy unit, n has an average value in the range 1.6–3.3 per 2-ethylhexyl group and m has an average value in the range 3.0–5.5 per 2-ethyl-hexyl group, and containing less than 1.5% by weight of unreacted 2-ethylhexanol; the said mixture being obtained by reacting 2-ethyl-hexanol in a first step with propylene oxide and in a second step the propoxylated mixture obtained with ethylene oxide. The alkoxylate mixture is a good cleaning surfactant and wetting agent and is also readily biodegradable.

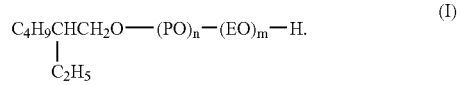

11 Claims, No Drawings

ALKOXYLATE MIXTURE AND ITS USE AS A CLEANING AGENT FOR HARD SURFACES

This case was filed under the Patent Cooperation Treaty on Jun. 19, 2003 and claims priority of Swedish patent application No. 0202100-4 filed Jul. 4, 2002.

The present invention relates to an alkoxylate mixture of 2-ethylhexanol produced by first propoxylating and then ethoxylating 2-ethylhexanol. The alkoxylate mixture has a low content of unreacted 2-ethylhexanol and contains normally between 2–20% of unethoxylated product. The alkoxylate mixture is a good cleaning surfactant and wetting agent and is also readily biodegradable.

2-Ethylhexanol is a suitable hydrophobic starting material for production of surfactants, especially nonionic alkoxylates, since it is low priced and readily available. Thus, ethoxylated 2-ethylhexanol with a low amount of unreacted alcohol is known from EP 845449 A1 to be a good surfactant for the cleaning of hard surfaces, and it is also readily biodegradable. According to this publication the amount of unreacted 2-ethylhexanol must be kept very low and this is achieved by using a narrow range catalyst for the ethoxylation reaction normally followed by a distillation of the ethoxylated product to remove the unreacted 2-ethylhexanol.

EP 681 865 B1 describes wetting agents consisting of mixtures of alkoxylated products, including products that have been first propoxylated and then ethoxylated, but where said mixtures always contain 30–60% of a propoxylated product. There are examples of products based on 2-ethylhexanol, but these are only pure propoxylates with 2, 6 or 10 PO units and also an alkoxylate with 8 PO and 6 EO units per 2-ethylhexyl group. However, the alkoxylate is not readily biodegradable.

In DE 42 12 592 A1 alkoxylates of PO and EO that are low-foaming wetting agents with foam-inhibiting properties are disclosed. However, 2-ethylhexanol is not mentioned as a suitable basis for such alkoxylates.

In EP 652 281 A1 an alkaline aqueous composition comprising nonionic surfactants that are propylene oxide-ethylene oxide derivatives of an alcohol with a linear or branched alkyl or alkenyl group and 2.5–7 moles of PO and 1–10 moles of EO per mole alcohol is described. The alkyl group contains 4–11 carbon atoms. This composition is used for the cleaning of the surface of articles such as fruit, vegetables or containers for food, or for chemical peeling of fruit or vegetables, metal working or cotton mercerization. None of the examples relates to any product based on 2-ethylhexanol, and the amount of PO in the products displayed in the examples is 4–7 PO. The high amount of PO is a disadvantage because of the poorer biodegradability of such products as compared to the products with less PO.

Similar alkoxylates are also disclosed in U.S. Pat. No. 4,965,014 and EP 34 194 B1, but in these publications the alkoxylates are only exemplified by products with predominantly longer alkyl chains.

The patent publications DD 292 146 A5 and DD 292 147 A5 describe wetting agents for finely ground materials, such as pulverized coal, which wetting agents are nonionic surfactants having an alkyl chain with 7–9 carbon atoms, 1–4 propyleneoxy (PO) units and 1.5–5 ethyleneoxy (EO) units. For the optimal surfactant the alkyl group is 2-ethylhexyl, the amount of PO is 2.5–3.5 and the amount of EO is 2–3. The very best wetting results were obtained with a product having 2.7 PO units and 2.1 EO units.

The object of the present invention is to provide an alkoxylated product based on 2-ethylhexanol with an excellent combination of a good wetting ability, a low foaming, a good performance as a cleaning surfactant for hard surfaces and a good biodegradability and a low toxicity. Further, the product should be produced by a process that is simple to perform, and which is not too costly.

Now it has surprisingly been found that these objects are fulfilled by an alkoxylate mixture with the formula

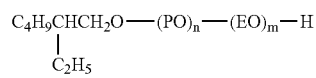

where PO is a propyleneoxy unit, EO is an ethyleneoxy unit, n has an average value in the range 1.6–3.3, preferably 1.6–2.4 and most preferably 1.8–2.3, per 2-ethylhexyl group and m has an average value in the range 3.0–5.5, preferably 3.6–4.6, per 2-ethylhexyl group, and containing less than 1.5% by weight of unreacted 2-ethylhexanol; the said mixture being obtained by reacting 2-ethylhexanol in a first step with propylene oxide and in a second step the propoxylated mixture obtained with ethylene oxide.

The alkoxylate mixture has a very good cleaning and wetting ability, and is excellent for the cleaning of hard surfaces. It is readily biodegradable, exhibits a low toxicity towards fish, Daphnia and nitrifying bacteria and a moderate toxicity towards algae.

To obtain the excellent performance properties of the product, it is important to add and react all the propylene oxide in the first step, so that the PO-block is adjacent to the 2-ethylhexoxy group. The product resulting after the ethoxylation, which is performed in the second step, will contain some unethoxylated product, i.e. 2-ethylhexanol that has only been propoxylated. Typically, this propoxylate will be present in an amount of between 2 and 20% by weight, normally between 5 and 15% by weight. The presence of propoxylates in the mixture improves the wetting ability and reduces the foaming. The total amount of PO in relation to the 2-ethylhexanol is also important. If the amount is too low, the performance of the product will not be optimal, and if the amount of PO is, too high, the biodegradability will be poorer. Also the balance between EO and PO is important for the performance, and in an especially preferred embodiment the molar ratio EO/PO is in the range 1.6–2.6.

The alkoxylate mixture could be used in aqueous cleaning compositions together with other conventional components, such as alkali and/or alkaline complexing agents, hydrotropes, other surfactants, thickening agents, solvents, colourants, soil antiredeposition agents, defrosting stabilizers, preservatives, corrosion inhibitors and foam regulators.

The invention also relates to a method for producing the alkoxylate mixture, where 2-ethylhexanol is reacted with 1.6–3.3, preferably 1.6–2.4 and most preferably 1.8–2.3, moles of propylene oxide per mole 2-ethylhexanol in the presence of a propoxylation catalyst at a temperature from 110° C. to 130° C. in a first step where the total amount of propylene oxide is allowed to react, whereupon the propoxylate mixture obtained, or the propoxylate mixture resulting after removal of unreacted 2-ethylhexanol, is reacted in a second step with 3.0–5.5, preferably 3.6–4.6, moles of ethylene oxide per mole 2-ethylhexanol propoxylate in the presence of an ethoxylation catalyst at a temperature from 60° C. to 180° C.

The propoxylation step can be performed in the presence of a propoxylation catalyst, preferably an alkaline catalyst selected from the group NaOH, KOH, NaOCH$_3$ and KOCH$_3$. For the ethoxylation step either an alkaline catalyst selected from the group NaOH, KOH, NaOCH$_3$ and KOCH$_3$, or a narrow range catalyst selected from the group Brönstedt acids, Lewis acids and Ca(OH)$_2$, could preferably be used. If a Brönstedt or Lewis acid is to be used in the ethoxylation step, the alkaline catalyst used in the first step should either be removed or neutralized before the start of the ethoxylation step. Preferably both the propoxylation and the ethoxylation step are performed in the presence of an alkaline catalyst, most preferably in the presence of KOCH$_3$.

The present invention is further illustrated by the following Examples.

EXAMPLE 1

In Table 1 some properties for alkoxylate mixtures according to the invention (=the first two products in Table 1) and alkoxylates used for comparison are collected.

The wetting ability was measured according to the modified Drave's test, where the sinking time in s is measured for a specified cotton yarn in approximately 0.1% surfactant solution.

The foam was measured as mm foam produced in a 500 ml measuring cylinder with 49 mm inner diameter from 200 ml of 0.5 g/l surfactant solution when the cylinder is turned around 40 times in one minute. The test was made at room temperature and the foam height was registered directly and after 1 minute.

For the test of cleaning efficiency a formulation in water containing 6% tetrapotassium pyrophosphate, 4% sodium metasilicate×5 H$_2$O, 5% alkoxylate and 2.4% sodium octyl-iminodipropionate was used. This formulation was diluted 1:30 with water.

Cleaning Test Procedure:

White painted plates were smeared with an oil-soot mixture obtained from diesel engines. 25 ml of the above-mentioned diluted formulation were poured onto the top of the oil-smeared plates and left there for one minute. The plates were then rinsed off with a rich flow of water. All solutions and the water were kept at a temperature of about 15–20° C. The cleaning efficiency was evaluated by measuring the amount of soil that had been removed from the surface, and where 100% represents a totally white and clean surface. The evaluation was performed by measuring the reflectance of the plates with a Minolta Chroma meter CR-200 reflectometer before and after the cleaning.

The amount of free 2-ethylhexanol in the alkoxylate mixture was determined by gas chromatography.

TABLE 1

| Product | Wetting Sinking time (s) | Foam height (mm) after 0 and 1 min | Foam height[5] (mm) after 0 and 1 min | Cleaning efficiency % removal | Free alcohol in alkoxylate (%) |
|---|---|---|---|---|---|
| 2-EH + 2PO + 4EO[1] | 7 | 20/0 | 10/1 | 80 | 1.1 |
| 2-EH + 2PO + 4EO[2] | 12 | | | | 0.4 |
| 2-EH + 4EO[3] | 90 | 12/0 | 25/1 | 40 | <0.5 |
| 2-EH + 4EO[4] | 125 | 37/0 | 70/20 | 20 | 11.4 |
| 2-EH + 2PO + 10EO | 194 | 75/17 | | | 0.2 |
| 2-EH + 3PO + 10EO | 100 | 84/8 | | | 0.1 |
| 2-EH + 4PO + 10EO | 83 | 83/5 | | | 0.05 |
| 2 EH + 4EO + 2PO | 61 | 8/0 | | | 1.7 |

2-EH = 2-ethylhexanol
[1]alkaline catalyst used in both propoxylation and ethoxylation step
[2]alkaline catalyst used in propoxylation step and narrow range catalyst used in ethoxylation step
[3]product produced according to EP 845 449 A1
[4]alkaline catalyst used for ethoxylation
[5]Foam height obtained using the cleaning formulation above From the results it is evident that the alkoxylate mixtures according to the invention have an excellent combination of good wetting ability, low foaming and high cleaning efficiency.

EXAMPLE 2

In Table 2 toxicity data for alkoxylate mixtures according to the invention and alkoxylates used for comparison are collected.

The biodegradability test was performed according to OECD 301 B.

The following toxicity tests have been used:
Fish (*Oncorhynchus mykiss*): OECD 203
Algae (*Scenedesmus subspicatus*): OECD 201
Daphnia magna: OECD 202
Nitrifying bacteria: ISO guidelines (1989) No. 9509

The following results were obtained.

TABLE 2

| Product | Biodegradability | Fish LC 50 (mg/l) | Algae EC50 (mg/l) | *Daphnia* EC50 (mg/l) | Nitrifying bacteria EC 50 (mg/l) |
|---|---|---|---|---|---|
| 2-EH + 2PO + 4EO | >60% | 42 | 7 | 48 | >1000 |
| 2-EH + 4EO[3] | >60% | 13 | 6 | 7 | 680 |
| 2-EH + 4PO + 10EO | <60% | | | | |

2-EH = 2-ethylhexanol
[3]product produced according to EP 845 449 A1

The alkoxylated mixture according to the invention is readily biodegradable, has a low toxicity towards fish and nitrifying bacteria and a moderate toxicity towards algae.

EXAMPLE 3

48 kmol of 2-ethylhexanol and 2% by weight, based on the alcohol, of KOCH$_3$ were charged into an alkoxylation reactor. The reactor was rinsed with nitrogen gas, and methanol was evaporated. The reactor was evacuated, the temperature increased to 120° C. and propylene oxide was charged in a total amount of 96 kmol. After completion of the reaction, the temperature was raised to 160° C. and ethylene oxide was charged in a total amount of 192 kmol. The resulting product was neutralized with acetic acid.

EXAMPLE 4

The same procedure as in Example 3 was followed, except that 1% by weight, based on the alcohol, of KOH was used for the propoxylation reaction, the intermediate propoxylate was neutralized and the ethoxylation step was performed at 70° C. in the presence of 0.3% by weight of $BF_3$, which is a catalyst that gives a narrow distribution of ethylene oxide units.

EXAMPLE 5

The cleaning efficiency of the product 2-ethylhexanol+ 2PO+4EO was compared to the products 2-ethylhexanol+ 2.7PO+2.1EO and 2-ethylhexanol+1.5 PO+3EO produced according to DD 292 147 A5.

To test the cleaning efficiency the same procedure was used as in Example 1. The cleaning formulation that was tested contained 5% nonionic surfactant, 6% tetrapotassium pyrophosphate, 4% sodium metasilicate×5 $H_2O$ and an amount of the hydrotrope sodium octyliminodipropionate sufficient to obtain a clear formulation.

TABLE 3

| Product | Amount hydrotrope (%) | Clarity interval (° C.) | Cleaning efficiency (% removal) |
|---|---|---|---|
| 2-EH + 2PO + 4EO | 2.4 | 0–53 | 80 |
| 2-EH + 2.7PO + 2.1EO | 3 | 0–47 | 50 |
| 2-EH + 1.5PO + 3EO | 2.6 | 0–49 | 60 |

From this test it is obvious that the cleaning efficiency of the product according to the invention is far superior to the cleaning efficiency of the similar products disclosed in DD 292 147 A5. Furthermore, the amount of the hydrotrope needed to obtain a clear solution was lower for the product according to the invention.

All three products were low-foaming.

The invention claimed is:

1. An alkoxylate mixture which comprises at least one alkoxylate of the formula

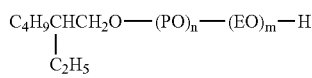

where PO is a propyleneoxy unit, EO is an ethyleneoxy unit, n has an average value in the range 1.6–2.4 per 2-ethylhexyl group and m has an average value in the range 3.6–4.6 per 2-ethylhexyl group, wherein the alkoxylate comprises less than 1.5% by weight of unreacted 2-ethylhexanol; said mixture being obtained by reacting 2-ethylhexanol in a first step with propylene oxide in order to obtain a propoxylated mixture, and in a second step ethoxylating the propoxylated mixture with ethylene oxide.

2. The alkoxylate mixture of claim 1, wherein the amount of 2-ethylhexyl propoxylate is between 2 and 20% by weight.

3. The alkoxylate mixture of claim 1 wherein n has an average value in the range 1.8–2.3 and m has an average value in the range 3.6–4.6.

4. The alkoxylate mixture of claim 1 wherein the molar ratio between ethylene oxide and propylene oxide is in the range 1.6–2.6.

5. A method of cleaning a hard surface which comprises treating said surface with a cleaning effective amount of the alkoxylate mixture of claim 1.

6. Method of producing an alkoxylate mixture which comprises reacting 2-ethylhexanol with 1.6–2.4 moles of propylene oxide per mole 2-ethylhexanol in the presence of a propoxylation catalyst at a temperature from 110° C. to 130° C. in a first step in order to obtain a propoxylate mixture followed by ethoxylating the propoxylate mixture in a second step with 3.6–4.6 moles of ethylene oxide per mole 2-ethylhexanol propoxylate in the presence of an ethoxylation catalyst at a temperature from 60° C. to 180° C.

7. The method of claim 6 wherein the propoxylation catalyst is an alkaline catalyst selected from the group NaOH, KOH, $NaOCH_3$ and $KOCH_3$.

8. The method of claim 7 the propoxylation and ethoxylation catalyst is $KOCH_3$.

9. The method of claim 6 wherein the ethoxylation catalyst is an alkaline catalyst selected from the group NaOH, KOH, $NaOCH_3$ and $KOCH_3$ or a narrow range catalyst selected from the group Brönstedt acids, Lewis acids and $Ca(OH)_2$, and mixtures thereof.

10. The method of claim 6 wherein the total amount of propylene oxide utilized in said first step is allowed to react.

11. The method of claim 6 wherein any unreacted 2-ethylhexanol is removed from the propoxylate mixture prior to ethoxylating said propoxylate mixture in said second step.

* * * * *